United States Patent [19]

Moore et al.

[11] Patent Number: 4,723,544

[45] Date of Patent: Feb. 9, 1988

[54] HEMISPHERICAL VECTORING NEEDLE GUIDE FOR DISCOLYSIS

[76] Inventors: Robert R. Moore, 4010 East Ave., Hayward, Calif. 94545; Steve R. Lamb, 2772 Sydney Way, Castro Valley, Calif. 94546

[21] Appl. No.: 883,561

[22] Filed: Jul. 9, 1986

[51] Int. Cl.⁴ .............................................. A61B 17/00
[52] U.S. Cl. .................................. 128/303 B; 604/116
[58] Field of Search ................... 128/303 B, DIG. 26; 604/51, 116

[56] References Cited

U.S. PATENT DOCUMENTS

| | | | |
|---|---|---|---|
| 2,697,433 | 12/1954 | Zehnder | 128/303 B |
| 3,941,127 | 3/1976 | Froning | 128/303 B |
| 3,964,480 | 6/1976 | Froning | 128/303 B |
| 4,230,117 | 10/1980 | Anichkov | 128/303 B |
| 4,350,159 | 9/1982 | Gouda | 128/303 B |
| 4,386,602 | 6/1983 | Sheldon et al. | 128/303 B |
| 4,463,758 | 8/1984 | Patil et al. | 128/303 B |
| 4,571,243 | 2/1986 | Froning et al. | 128/303 B |
| 4,638,799 | 1/1987 | Moore | 128/303 B |

*Primary Examiner*—Gene Mancene
*Assistant Examiner*—Cary E. Stone
*Attorney, Agent, or Firm*—Bielen and Peterson

[57] ABSTRACT

A vectographic guide device for an injection needle in discolysis procedures the device having a target structure and a positioning component on which a guide mount for a needle guide is attached, the target structure and positioning component being supported by an adjustment mechanism attached to an operating table for locating and the target structure and positioning component is a desired location over to operating table, the positioning component having a tracking mechanism to locate the guide mount on the locus of a partial spherical surface area having a center coincident with a target point defined by the target structure.

9 Claims, 10 Drawing Figures

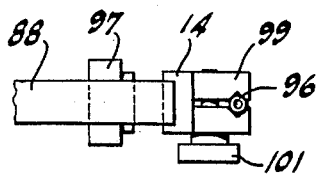
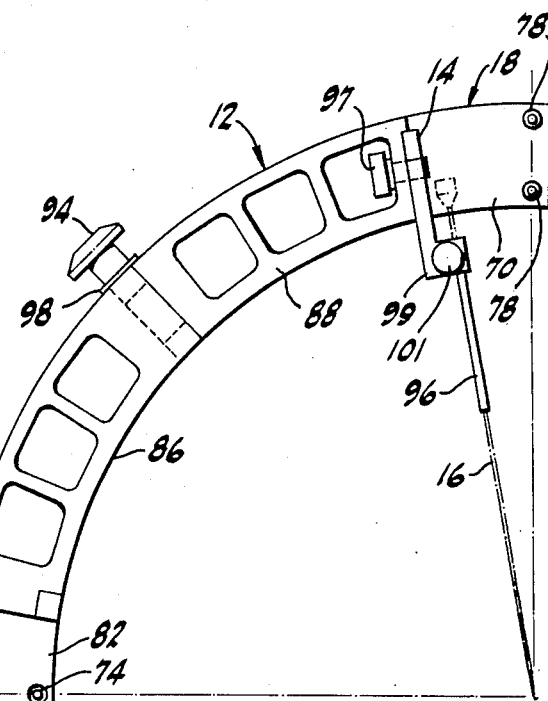
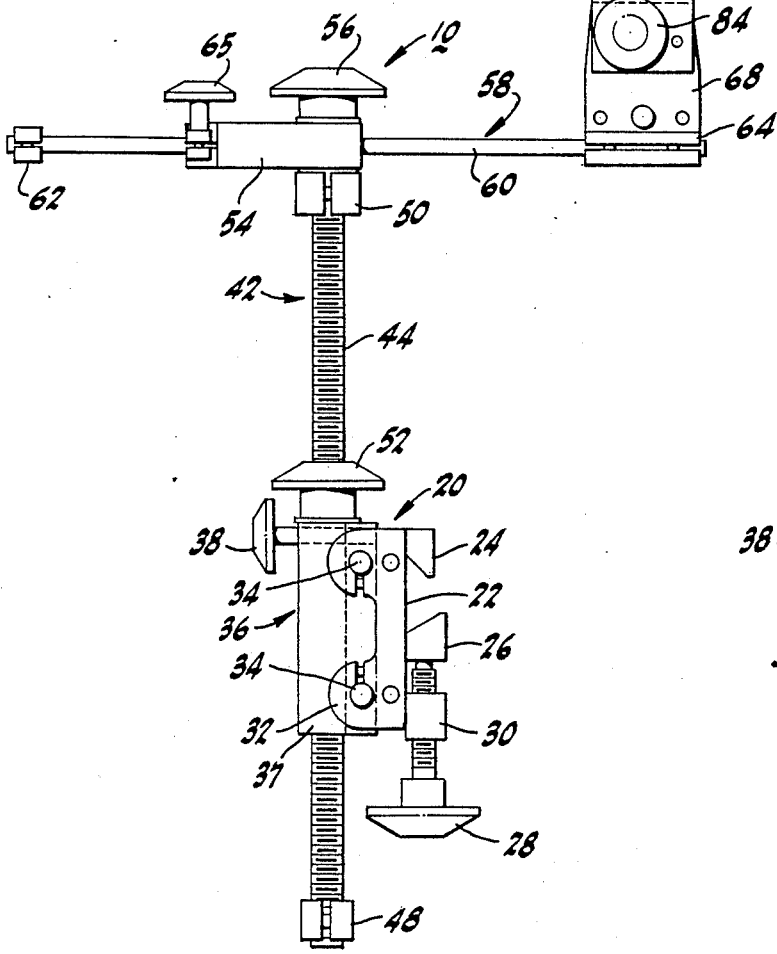
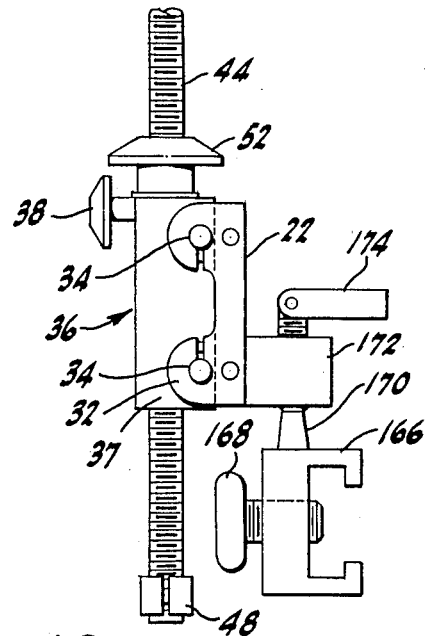

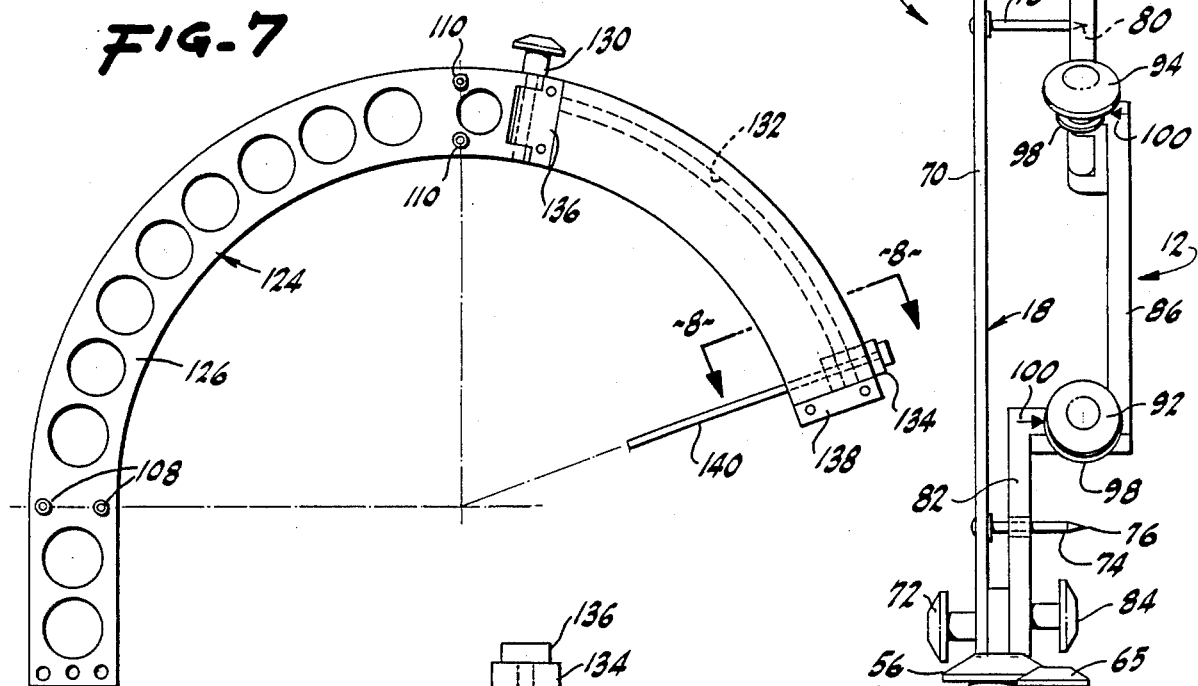
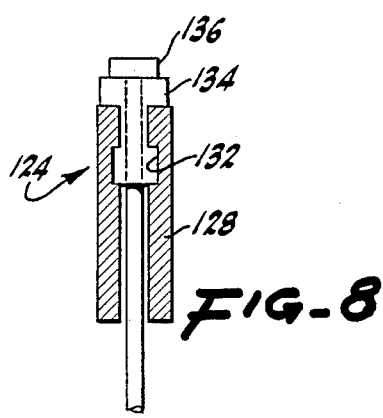
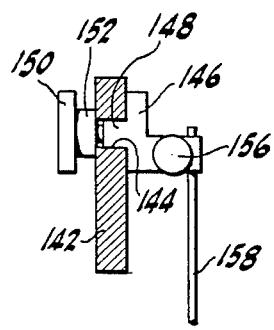
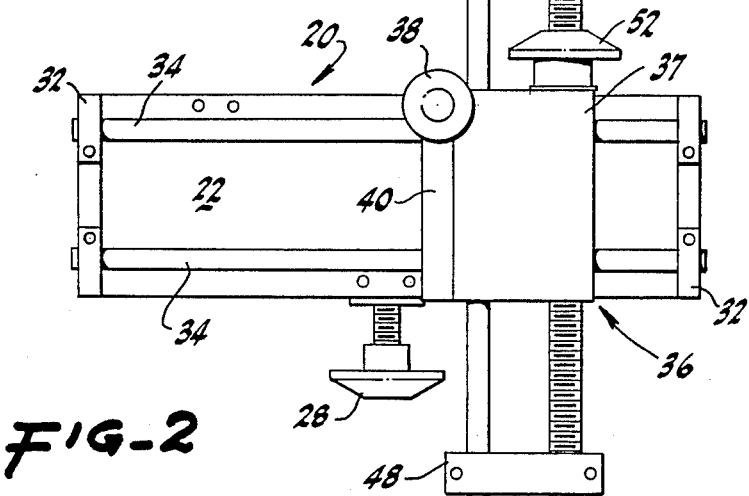

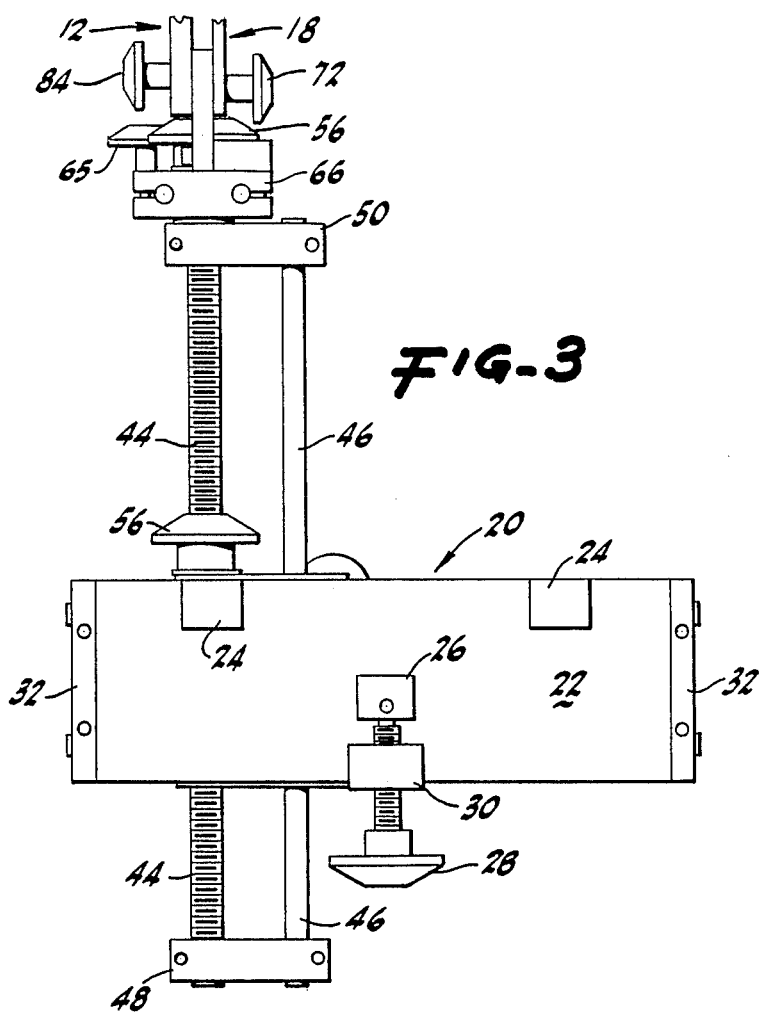
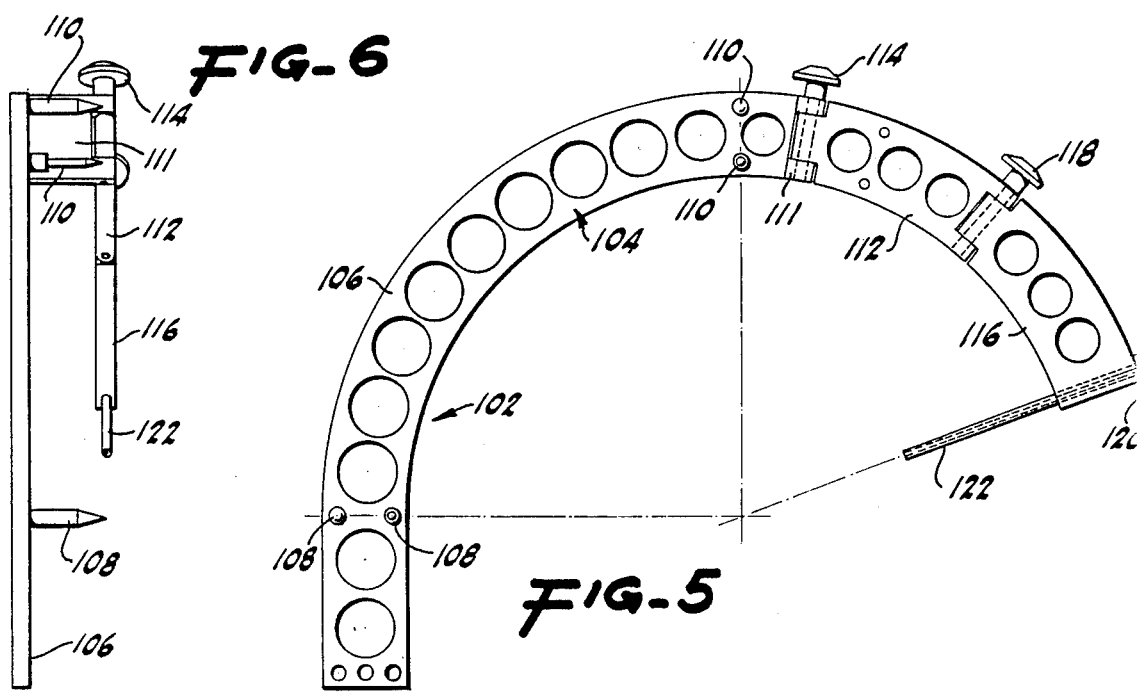

HEMISPHERICAL VECTORING NEEDLE GUIDE FOR DISCOLYSIS

BACKGROUND OF THE INVENTION

This invention relates to a needle guide apparatus for discolysis procedures for the accurate insertion of an elongated injection needle into a select intervertebral disc for injection of a lysing agent or dye into the disc. The apparatus of this invention is particularly useful to aid chemonucleolysis procedures for non-surgical treatment of a herniated invertebral disc. The invention is of the type disclosed in the application of Robert Moore, entitled, "Needle Guide Apparatus for Discolysis Procedures" Ser. No. 744,392 filed, June 13, 1985 now U.S. Pat. No. 4,638,799.

As discussed in that application, certain chemicals have been discovered that dissolve nucleus pulposus material, the gelatinous substance within a vertebral disc. These agents, known generally as lysing agents, when injected into a herniated disc, cause the gelatinous material to dissolve, relieving pressure on nearby spinal nerves. Of the two principal applicable lysing agents, chymopapain and collagenase, chymopapain is used most frequently. Chymopapain is an enzyme derivative from papaya and has been found to dissolve the material forming the nucleus pulposus, without adverse affect on the surrounding annulus fibrosis or thin top and bottom plates of hyaline cartilage. Success from intradiscal injection of chymopapain has provided, in many cases, an effective alternative to open back surgery for removal of repair of a herniated disc by a laminectomy procedure.

A major problem with the chemonucleolysis procedures however, is the accurate placement of the needle into the nucleus pulposus of the herniated disc. Prior to the Moore apparatus needle placement was in part trial and error, often requiring up to one hour of a treating physician's time to locate the tip of the needle at the desired point within the disc. In addition to the tedium of the procedure and wasted time, misplacement or repeated perforation can be harmful to the patient. Prior devices to guide and locate the needle, as the device of the Moore reference, have been devised to direct the needle to the desired spot in the disc. Such devices, however, use complicated structures that in part restrict the angle options available to the surgeon. The needle guide of this invention expands the available angle option with a simplified structure using spherical vectoring techniques.

The improved needle guide is primarily used in discolysis procedures, but may be used in other procedures particularly where a substance is injected into a disc or other internal regions where both depth of penetration and direction of entry are critical.

SUMMARY OF THE INVENTION

The improved needle guide apparatus of this invention is devised to aid a physician in accurately guiding and locating an injection needle into an invertebral disc, particularly for chymonucleosis procedures during diagnosis and treatment of a herniated disc. Proper needle placement is important for injection of a dye and subsequent injection of a lysing agent, or in some situations, injection of a combined dye and lysing agent solution.

Chemical excision of herniated nucleus pulposus by injection of a lysing agent, such as chymopapain or collagenase, is an effective alternative to surgery. A most difficult step in the chumonucleosis procedure is accurate insertion and placement of the needle through the annulus fibrosis and into the nucleus pulposus. Because a direct posterior approach will penetrate the spinal cord, and cause possible nerve damage, a more difficult lateral approach is recommended. For discs between the third and forth, and forth and fifth lumbar vertebrae, a 45° angle from the direct posterior axis is preferred, although some surgeons recommend a 55° angle.

The most commonly affected disc is between the fourth and fifth lumbar vetabrae. The second most commonly affected disc, however, is between the fifth lumbar vertebrae and the sacrum, a particularly difficult disc to reach. For this disc a needle positioned at an angle of 45° from the horizontal place of the sagittal axis must also be positioned at a 30° angle from the cross sectional plane of the spinal column for a diagonal entry into the disc center.

This compound angle requires a stereotaxic vectoring device for accurate guide and location of a needle tip. While the prior device of Moore provides for one or more angles of insertion according to fixed guides of predetermined orientation, it allows only limited discretion to the surgeon in defining the optimum angle of entry for a particular patient or a particular condition.

The hemispheric vectoring guide apparatus of this invention in certain embodiments permits a target point at the spine to be reached from virtually any direction normal to a hemispherical surface. For most chymoneucleosis procedures, this full range is not necessary, and a preferred embodiment limits this range to all of the useful vectoral directions by a more compact and accurate structure.

The hemispheric vectoring guide apparatus includes a mount for connecting the apparatus to an operating table, plus horizontal and vertical adjustment means for positioning a target structure and vectoring component. The target structure comprises a first sighting device on a horizontal axis and a second sighting device on a vertical axis in the plane of the horizontal axis such that a intersection point of the two axes defines the target point. The vectoring component is preferably constructed with first second and third interconnected arcuate members although a single articulating arcuate member with a slide component may be used. The interconnections of the first and second, and the second and third arcuate members are pivotal on axes radially directed to the target point defined by the complimentary target structure. The pivotal connection allows the second and third segments to articulate, whereby the distal end of the vectoring component to which a needle holder is attached is orientable at any point on a spherical surface within a limited field. This enables the physician to select the precise direction desired for entry of his needle. Each selection will position the needle holder such that the distance to the target point is identical. The physician adjusts the target structure using a floroscope or other radioscopic instrument to center and align the target structure, using the sighting devices, over the site of interest, for example the center of the spinal disc to be penetrated. The physician selects his entry angle using the vectoring component, adjusts the depth of penetration from the known standard and makes his insertion.

The depth of penetration will determine the precise location of the needle end, which can be predetermined to arrive, before, after or at the centerpoint location.

For the lumbosacral disc, the compound angle is devised to permit a guide needle to penetrate the upper edge of the disc, allowing a smaller injection needle to concentrically feed through the guide needle and curve into the center of the disc, using a double needle technique. The more complicated angle and technique is necessary to avoid the protective iliac crest of the sacrum. Proper centering of the target structure over the center of the disc and positioning the vectoring component to the desired compound angle position will accurately situate the guide needle end on line for the disc axis, with a curve of the injection needle necessary to situate the needle end centrally between the hyaline cartilage plates.

Once the needle guide apparatus is properly positioned and checked, the inserted needle will be guided to the proper location for injection. Final positioning may be determined through feel and subsequent x-ray imaging. These precision techniques are substantially aided by use of the accurate positioning and orientation devices described herein.

BRIEF DESCRIPTION OF THE DRAWINGS

FIG. 1 is a side elevational view of the hemispheric vectographic guide device of this invention.

FIG. 2 is a side elevational view of the device of FIG. 1.

FIG. 3 is an opposite side elevational view partially fragmented of FIG. 1.

FIG. 4 is an enlarged partial top view of the end of the guide device of FIG. 1.

FIG. 5 is a partial view of an alternate embodiment of a portion of the device of FIG. 1.

FIG. 6 is an end view of the alternate embodiment of FIG. 5.

FIG. 7 is a side view of an alternate positioning component for the device of FIG. 1.

FIG. 8 is a cross sectional view taken on the lines 8—8 in FIG. 6.

FIG. 9 is a cross sectional view of an alternate slide component.

FIG. 10 is a side elevational view of an alternate mounting means for the guide device.

DETAILED DESCRIPTION OF THE PREFERRED EMBODIMENTS

Referring to FIG. 1, the vectographic guide device designated generally by the reference numeral 10, is shown in a side elevational view to illustrate the hemispherical positioning component 12 for the actual guide mount 14 for the injection needle 16 shown in phantom. Behind the positioning component 12 is a target structure 18. The cooperative arrangement of the positioning component 12 and the target structure 18 in the embodiment of FIG. 1 is particularly designed for discolysis procedures where the guide element need sweep over only a portion of a hemispherical locus. If greater coverage is required, an embodiment as in the schematic illustration of FIG. 4 may be preferred, where a greater portion of a hemispherical locus is covered.

The hemispheric, vectographic guide device 10 of this invention is constructed with a mounting mechanism 20 for affixing the device to a side rail of an operating table (not shown). The mechanism 20 includes a backing plate 22 having a pair of spaced upper clamp members 24, shown also in FIG. 3, which wedge over the top of the side rail, and a displaceable centrally positioned clamp member 26, which wedges under the bottom of the rail. On tightening a turnscrew 28 threadably mounted in a block 30, the backing plate 22 is drawn into alignment firmly against the rail.

The backing plate 22 includes end plates 32 for end support of a pair of displaced guide rods 34 on which is mounted carriage assembly 36. The carriage assembly 36 is constructed with a carriage block 37 having internal bearing sleeves which engage the rods 34 allowing the block 37 to freely track along the length of the rods 34. A stop screw 38 passes through a threaded hole in a step down segment 40 of the block 37 to engage the backing plate 22 when the stop screw is tightened. This locks the carriage to the backing plate at the desired position relative to the length of the operating table.

In conjunction with the carriage feature of the block 30 are a vertically oriented bearing sleeve and screw passage for engagement of a vertically displaceable jig structure 42 constructed with an elongated turnscrew 44 and parallel guide rod 46 both clamped to a lower bar 48 and an upper bar 50. A turn collar 52 rotatably mounted to the carriage block 37 engages the turnscrew 44. Rotation of the turn collar 52 raises or lowers the jig structure 42 relative to the block.

The upper bar 50 forms a support platform for a guide block 54 which is pivotally secured to the bar 50 by a threaded clamping knob 56, which engages a segment of the turnscrew 44 extending above the upper bar 50. The pivotal connection enables a slide support 58 carrying the needle guide positioning component 12 and the target structure 18 to rotate in a horizontal plane relative to the vertically adjustable jig structure to compensate for a skewed orientation of the patient on the operating table. The slide support 58 is constructed with two parallel rods 60 connected at one end to a cross bar 62 and connected at their other end to a mount 64. The rods slide in the guide block 54 which includes a clamp screw 65 to lock the slide support 58 in a desired position. The mount 64 has a step structure 66 for attaching and orienting an attachment arm 68. The attachment arm 68 provides a support for the positioning component 18 and the target structure 18.

The target structure comprises an arcuate member 70 secured to the attachment arm 68 by a knobbed clamping screw 72. The arcuate member 70 has a pair of lower parallel sights 74 with pointed ends 76 arranged to demarcate a horizontal axis and a pair of upper parallel sights 78 with pointed ends 80 arranged to demarcate a vertical axis intersecting the demarcated horizontal axis. The point of intersection is the target point for purposes of targeting the tool mount 14 at the end of the positioning component 12.

The positioning component 12 is constructed with three arcuate segments, a first fixed segment 82, which is clamped to the attachment arm 68 by a turnscrew 84, a central segment 86 connected at an end to the fixed segment 82, and an end segment 88 connected at one end to the central segment 86 and supporting the tool mount 14 at its distal end.

The fixed segment 82 is juxtaposed to the target structure on the opposite side of the attachment arm and includes holes 90 through which the horizontal sights 74 project for developing the horizontal radiosopic line of sight. The end of the fixed 82 is pivotally connected to the end of the central segment by a pivot clamping pin 92 having an axis oriented to intersect the target point. The clamping pin 92 allows the central segment to articulate on the pivot axis with respect to the fixed segment, and on tightening the clamping pin 92 fixes the relative position of the central segment with respect to the fixed segment. Similarly, the end segment 88 is connected to the central segment 86 by a pivot clamping pin 94 also having an axis directed to the target point. The clamping pin 94 on tightening fixes the position of the end segment relative to the central segment.

The structure of segments are stepped as shown in FIG. 2 to orient the guide mount 14 in the plane of the intersecting target lines when the positioning component 12 is aligned with the target structure 18 for convenient reference prior to desired repositioning according to the angular specifications of a particular procedure.

The dual articulation permits the tool mount to be located anywhere on a delimited spherical surface locus as limited by the reach of the positioning component. At all points in the field, the guide mount is oriented in order that a tool guide 96, such as the needle guide shown in FIG. 1, is directed at the target point. At all positions, the guide mount 14 is equally distant from the target point as it follows the locus of a spherical surface relative to the center point of the sphere which is coincident with the target point.

The guide mount 14 in FIGS. 1 and 4 is a needle guide support that is mounted to the butt end of the end segment 88 by a thumbscrew 97. The guide mount 14 has an end clamp 99 with a smaller thumb screw 101 for clamping the needle guide 96 in position. The needle is longitudinally adjustable to permit location of the guide according to the length of the needle and the desired final position of the needle tip. It is understood that the guide mount 14 may be of different configuration where the tool is a device other than a needle.

As guides for the physician a marked disk 98 rotates with the articulating member relative to marker 100 on the connecting element to indicate relative position by references that can be correlated with entry angles using a correlation chart (not shown). The device of this invention allows the physician to arrange for injections according to his own entry specifications as well as in conformity to traditional trajectories.

While the embodiment of FIGS. 1–4 is preferred for discolysis procedures, a modified target and positioning component as shown in FIGS. 5 and 6 may be desired. In the partial embodiment of FIGS. 5 and 6 only the targeting and positioning component 102 differ, the remaining support structure (not shown) remaining the same. The combined target and positioning component 102 includes an arcuate support arm 104 having three segments. The first segment 106 is attached to the attachment arm 68 (not shown) and includes horizontal target pins 108 and vertical target pins 110. At the distal L-configured end 111 of the fixed first segment 106 is an articulating central segment 112 connected at one end to the fixed segment by a pivot clamp 114 having a pivot axis directed to the target point formed at the intersection of target lines from the target pins 108 and 110. At the end of the central segment 112 is an end segment 116 connect at one end to the fixed segment by a pivot clamp 118, again with a pivot axis directed at the target point. The distal end of the end segment 116 supports guide mount 120 for a needle guide 122 with an axis oriented at the target point. Similarly, the dual articulation orients the needle guide equidistant from and directed at the target point from whatever vector selected by the surgeon.

As a further embodiment, a vectographic guide device may include the adjustment structure of the embodiment of FIGS. 1–4 with a substitute target structure and positioning component 124 as shown in FIGS. 7 and 8. The positioning component includes a first segment 126 with target elements as in FIG. 5, the first segment being fixed to the support mount 64. The positioning component includes a second split segment 128 pivotally connected at one end to the end of the first segment by a clamping pivot pin 130. The axis of pivot is directed toward the target point enabling the second arcuate segment to sweep a partial surface of a sphere centered on the target point. On the arcuate second segment is a guide track 132 for a slide support 134 which tracks an arcuate path centered about the target point between the pivot end spacer 136 to the distal end spacer 138. A guide mount 140 is attached to the slide support 134 to direct a surgical instrument toward the target point at all positions within the delimited range of the articulating segment and sliding support. As in the former embodiments the tool mount is properly oriented and equidistant from the target point at all positions within its range.

As a further modified embodiment, the device of FIG. 7 can be constructed with an end segment 142 as shown in FIG. 9 that is not split, but has instead an arcuate slot 144 through the end segment that is comparable to the track 132 in FIG. 8. With this construction, a slider 146 with a side projection 148 that engages the slot 144 can track along the slot and be clamped in a select position by the opposed thumb screw 150 and washer 152. A needle clamp screw 156 clamps a needle guide 158 in a similar manner as in FIG. 1.

Other modifications in the vectographic guide device may be made to improve its versitility. For example, where it is difficult to properly orient a patient on a table because the patient is unresponsive or has added complications requiring certain positions to be avoided, then an alternate table mounting means may be preferred. As shown in FIG. 10 a side rail bracket 166 slides onto a conventional side rail (not shown) and is secured by a clamping knob screw 168. Fixed to the top of the bracket 166 is a ball pedestal 170, which is engaged by a ball socket structure 172 that has a clamping crank 174 for fixing the relative desired position of the socket structure to the bracket. The socket structure 172 is attached to the backing plate 22 for slidably attaching the carriage assembly 36, as in the FIG. 1 embodiment.

The ball and socket component allows the mounting mechanism to tilt to allow the needle guide positioning component (not shown), to properly align with the patient's back in discolysis procedures or along with a planar frame of reference that is tilted from the normal to the table in other medical procedures.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A vectographic guide device particularly adapted for use as a needle guide for discolysis procedures for directing an injection needle into a spinal disc of a patient on an operating table with the patient having a saggital axis longitudinally oriented to the table, the guide device comprising:
- (a) mounting means for connecting the guide devide to the side of an operating table;
- (b) a guide mount having means for attaching a tool guide having a specific directional orientation;
- (c) a positioning component on which said guide mount is attached;
- (d) a target structure having target means for targeting a point in three dimensional space;
- (e) adjustable support means supporting said target structure and said positioning component, said support means being connected to said mounting means locating said positioning component and target structure over the operating table in a desired position, wherein said target structure has targeting elements arranged on said structure to define a target point, and wherein said positioning component has spherical surface tracking means for selectively positioning said guide mount on a delimited spherical surface locus equidistant from the target point and directionally oriented toward said target point, and further, wherein said adjustable support means comprises first carriage means connected to the mounting means for tracking the target structure and positioning component in a first horizontal direction, a screw operated jig means connected to the first carriage means for raising and lowering the target structure and positioning component, pivot means connected to the jig means for angular pivot of the target structure and positioning component in a horizontal plane and second carriage means connected to the pivot means for tracking the target structure and positioning component in a second horizontal direction.

2. A vectographic guide device particularly adapted for use as a needle guide for discolysis procedures for directing an injection needle into a spinal disc of a patient on an operating table with the patient having a sagittal axis longitudinally oriented to the table, the guide device comprising:
- (a) mounting means for connecting the guide device to the side of an operating table;
- (b) a guide mount having means for attaching a tool guide having a specific directional orientation;
- (c) a positioning component on which said guide mount is attached;
- (d) a target structure having target means for targeting a point in three dimensional space;
- (e) adjustable support means supporting said target structure and said positioning component, said support means being connected to said mounting means locating said positioning component and target structure over the operating table in a desired position, wherein said target structure has targeting elements arranged on said structure to define a target point, and wherein said positioning component has spherical surface tracking means for selectively positioning said guide mount on a delimited spherical surface locus equidistant from the target point and directionally oriented toward said target point, and further, wherein the positioning component comprises an arcuate arm structure having first, second and third segments wherein said first segment is fixed to said adjustable support means, said second segment is pivotally connected to said first segment on a first pivot axis intersecting said target point, and said third segment is pivotally connected to said second segment on a second pivot axis intersecting said target point angularly displaced from said first axis, said third segment having a distal end on which is mounted said guide mount.

3. The vectographic guide device of claim 2 wherein said target structure comprises said first fixed segment of the positioning component.

4. The vectographic guide device of claim 3 wherein said first segment has an arcuate portion exceeding 90 degrees.

5. The vectographic guide device of claim 4 wherein said target elements comprises a first pair of projecting parallel pins arranged on said first segment in a horizontal plane with pointed ends defining a first line and a second pair of projecting parallel pins arranged on said first segment in a vertical plane with pointed ends defining a second line intersecting the first line defining a target point as the point of intersection.

6. The vectographic guide device of claim 2 wherein said target structure comprises an arcuate arm juxtaposed to said positioning component, said target structure having a first pair of projecting parallel pins arranged in a horizontal plane with pointed ends defining a first line and second pair of projecting parallel pins arranged in vertical plane with pointed ends defining a second line intersecting said first line defining a target point at the point of intersection.

7. A vectographic guide device particularly adapted for use as a needle guide for discolysis procedures for directing an injection needle into a spinal disc of a patient on an operating table with the patient having a sagittal axis longitudinally oriented to the table, the guide device comprising:
- (a) mounting means for connecting the guide device to the side of an operating table;
- (b) a guide mount having means for attaching a tool guide having a specific directional orientation;
- (c) a positioning component on which said guide mount is attached;
- (d) a target structure having target means for targeting a point in three dimensional space;
- (e) adjustable support means supporting said target structure and said positioning component, said suport means being connected to said mounting means locating said positioning component and target structure over the operating table in a desired position, wherein said target structure has targeting elements arranged on said structure to define a target point, and wherein said positioning component has spherical surface tracking means for selectively positioning said guide mount on a delimited spherical surface locus equidistant from the target point and directionally oriented toward said target point, and further, wherein said spherical surface tracking means comprises a positioning structure having a first segment attached to the adjustable support means and an arcuate second segment with a first end pivotally connected to the first segment on a pivot axis intersecting said target point, said arcuate second segment having a slide support and a tracking means for tracking an arcuate path about the target point as centerpoint, said guide mount being carried by said slide support.

8. A vectographic guide device particularly adapted for use as a needle guide for discolysis procedures for directing an injection needle into a spinal disc of a patient on an operating table with the patient having a sagittal axis longitudinally oriented to the table, the guide device comprising:
- (a) mounting means for connecting the guide device to the side of an operating table;
- (b) a guide mount having means for attaching a tool guide having a specific directional orientation;
- (c) a positioning component on which said guide mount is attached;
- (d) a target structure having target means for targeting a point in three dimensional space;
- (e) adjustable support means supporting said target structure and said positioning component, said support means being connected to said mounting means locating said positioning component and target structure over the operating table in a desired position, wherein said target structure has targeting elements arranged on said structure to define a target point, and wherein said positioning component has spherical surface tracking means for selectively positioning said guide mount on a delimited spherical surface locus equidistant from the target point and directionally oriented toward said target point, and further, wherein said mounting means for connecting the guide device to the side of an operating table includes a clamp member having means to clamp the clamp member to the side rail and ball interconnecting means for interconnecting said clamp member and said adjustable support means with universal ball joint pivot within a delimited range.

9. A vectographic guide device particularly adapted for use as a needle guide for discolysis procedures for directing an injection needle into a spinal disc of a patient on an operating table with the patient having a sagittal axis longitudinally oriented to the table, the guide device comprising:
- (a) mounting means for connecting the guide device to the side of an operating table;
- (b) a guide mount having means for attaching a tool guide having a specific directional orientation;
- (c) a positioning component on which said guide mount is attached;
- (d) a target structure having target means for targeting a point in three dimensional space;
- (e) adjustable support means supporting said target structure and said positioning component, said support means being connected to said mounting means locating said positioning component and target structure over the operating table in a desired position, wherein said target structure has targeting elements arranged on said structure to define a target point, and wherein said positioning component has spherical surface tracking means for selectively positioning said guide mount on a delimited spherical surface locus equidistant from the target point and directionally oriented toward said target point, and further, wherein said support means is adjustable to a variety of positions, with said positioning component and target structure arranged to maintain the position of said guide mount equidistant and directionally oriented toward said target point at all positions of said support means and at all positions of said guide mount on said dilimited spherical surface locus.

* * * * *